(12) United States Patent
Krentler et al.

(10) Patent No.: US 10,744,296 B2
(45) Date of Patent: Aug. 18, 2020

(54) GAS DEMAND DEVICE, METHOD OF INSTALLATION, GAS DELIVERY SYSTEM, AND METHOD OF USE

(71) Applicant: L'Air Liquide Societe Anonyme Pour L'Etude Et L'Exploitation Des Procedes Georges Claude, Paris (FR)

(72) Inventors: Stephen Bruce Krentler, Bethlehem, PA (US); Hans Irr, Bethlehem, PA (US); Barry Wood, Slough (GB); Paul N. Trevena, Maidenhead (GB)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 790 days.

(21) Appl. No.: 15/255,858

(22) Filed: Sep. 2, 2016

(65) Prior Publication Data
US 2017/0065790 A1    Mar. 9, 2017

Related U.S. Application Data

(60) Provisional application No. 62/214,387, filed on Sep. 4, 2015.

(51) Int. Cl.
*A61M 16/20* (2006.01)
*A61M 16/06* (2006.01)
(Continued)

(52) U.S. Cl.
CPC ...... *A61M 16/207* (2014.02); *A61M 16/0057* (2013.01); *A61M 16/0666* (2013.01);
(Continued)

(58) Field of Classification Search
CPC .............. A61M 11/06; A61M 15/0086; A61M 15/0093; A61M 16/00; A61M 16/0006;
(Continued)

(56) References Cited

U.S. PATENT DOCUMENTS 4,054,133 A * 10/1977 Myers .................. A61M 16/20
128/204.26
4,802,507 A    2/1989 Willson
(Continued)

FOREIGN PATENT DOCUMENTS

WO    WO 96/40336    12/1996
WO    WO 01/21240    3/2001

OTHER PUBLICATIONS

International Search Report and Written Opinion for PCT/US2016/050170, dated Nov. 23, 2016.

*Primary Examiner* — Annette Dixon
(74) *Attorney, Agent, or Firm* — Christopher J. Cronin

(57) ABSTRACT

A gas demand device cycles through five successive operation phases: gas is prevented from flowing through the timing gas and demand gas flow paths; gas is allowed to flow through the timing gas flow path and gas is prevented from flowing through the demand gas flow path; gas is allowed to flow through the timing gas and demand gas flow paths; gas is prevented from flowing through the timing gas flow path and gas is allowed to flow through the demand gas flow path; and gas is prevented from flowing through the timing gas and demand gas flow paths.

1 Claim, 13 Drawing Sheets

(51) Int. Cl.
*A61M 16/00* (2006.01)
*A61M 16/08* (2006.01)
A62B 7/14 (2006.01)
A62B 9/02 (2006.01)
B64D 13/06 (2006.01)

(52) U.S. Cl.
CPC . *A61M 16/0816* (2013.01); *A61M 2205/3355* (2013.01); *A62B 7/14* (2013.01); *A62B 9/02* (2013.01); *B64D 2013/0677* (2013.01); *B64D 2013/0681* (2013.01)

(58) Field of Classification Search
CPC .......... A61M 16/0012; A61M 16/0051; A61M 16/024; A61M 16/0677; A61M 16/0858; A61M 16/107; A61M 16/127; A61M 16/20; A61M 16/206; A61M 16/207; A61M 16/208; A61M 16/209; A61M 2016/0021; A61M 2016/0039; A61M 2202/0007; A61M 2202/0208; A61M 2202/03; A61M 2205/8225; A62B 15/00; A62B 9/022; A62B 9/027; B64D 10/00; Y10T 137/2012; Y10T 137/2544
See application file for complete search history.

(56) References Cited

U.S. PATENT DOCUMENTS

| | | | | |
|---|---|---|---|---|
| 5,360,000 | A * | 11/1994 | Carter | A61M 16/20 128/204.26 |
| 5,666,945 | A * | 9/1997 | Davenport | A61M 16/20 128/200.14 |
| 6,116,242 | A * | 9/2000 | Frye | A61M 16/00 128/205.24 |
| 6,425,396 | B1 | 7/2002 | Adriance et al. | |
| 6,484,721 | B1 | 11/2002 | Bliss | |
| 6,752,152 | B2 | 6/2004 | Gale et al. | |
| 6,910,510 | B2 | 6/2005 | Gale et al. | |
| 7,089,938 | B2 | 8/2006 | Gale et al. | |
| 7,708,016 | B2 * | 5/2010 | Zaiser | A61M 16/00 128/200.24 |
| 8,276,584 | B2 | 10/2012 | Tatarek | |

* cited by examiner

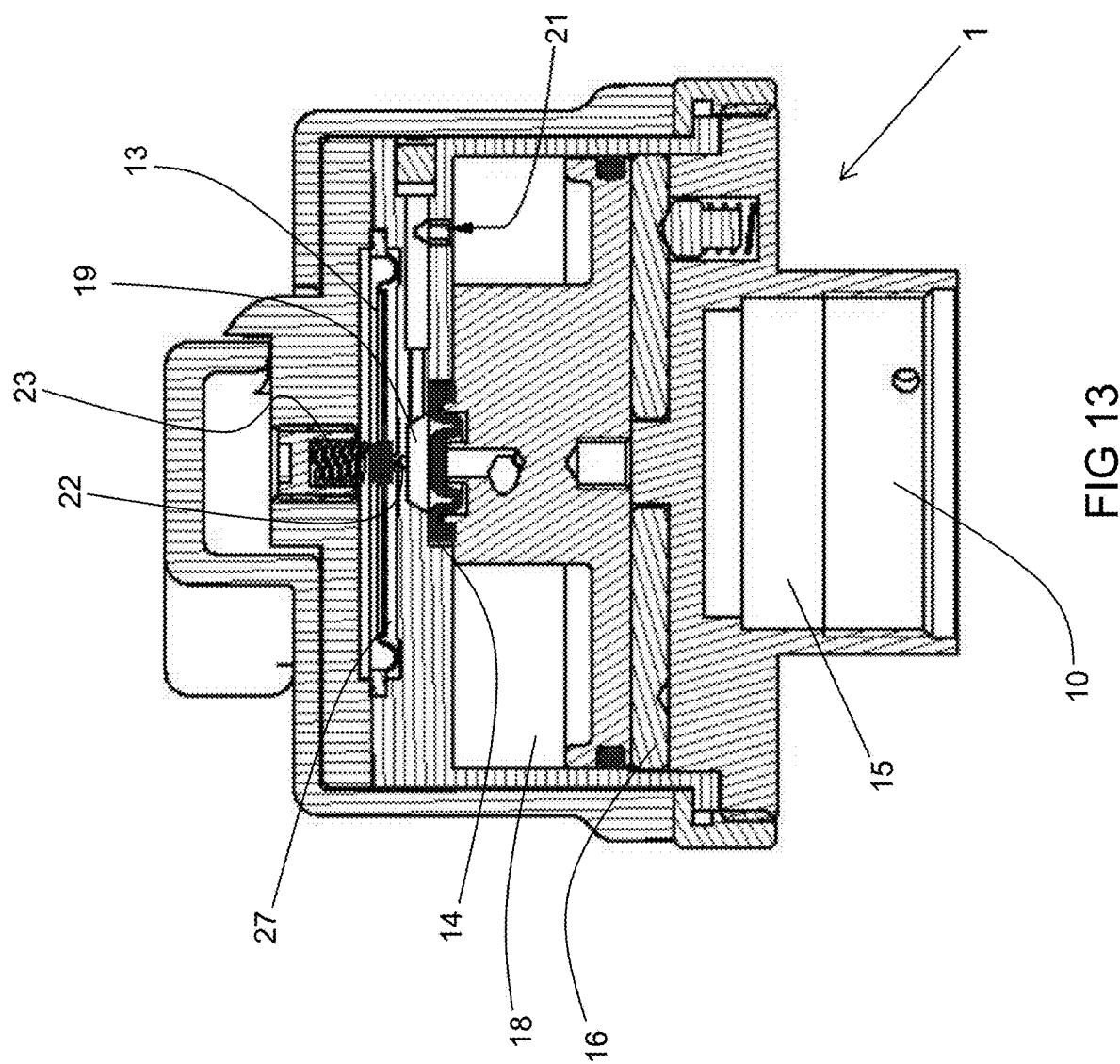

GAS DEMAND DEVICE, METHOD OF INSTALLATION, GAS DELIVERY SYSTEM, AND METHOD OF USE

CROSS-REFERENCE TO RELATED APPLICATIONS

This application claims the benefit of priority under 35 U.S.C. § 119 (e) to U.S. Provisional Patent Application No. 62/214,387, filed Sep. 4, 2015, the entire contents of which are incorporated herein by reference.

BACKGROUND

Field of the Invention

The present invention relates to gas demand devices.

Related Art

Gas demand devices are used to provide controlled amounts of gas for inhalation by persons. Two examples of these kinds of devices include oxygen demand devices for patient oxygen therapy and oxygen demand devices for airplane crew and/or passengers in low oxygen or low pressure environments aboard aircraft.

Oxygen demand devices in the home healthcare market have for many years improved the usable duration of supply vessels (cylinders, tanks, containers, etc.) over continuous flow devices (regulators, flowmeters, liquid oxygen dewars, etc.) while still adequately satisfying the clinical needs of the oxygen patent. These systems typically only provide oxygen to the user during the inhalation portion of a breath, optimally in the first half of the user's inhalation.

Initially most devices were electronic using batteries as a power source. Later, pneumatic device using the pressure in the supply vessel as a power source became the preferred systems due to no need for batteries, smaller size and ease of use. Both types afforded the oxygen patient to ambulate for longer periods of time and/or require less frequent oxygen supply refills.

Weight reduction in aerospace is a constant goal to reduce fuel consumption, increase range and improve safety. Current systems for on-board oxygen provide continuous flow oxygen which limits supply duration, requires the maximum size supply vessel storage space will allow regardless if used which in most flights they are not and can limit aircraft range.

Some home healthcare demand systems have been tried in commercial aviation market with limited acceptance and success. Most were not durable enough for the rigors of the commercial aviation market or provide inadequate interface with the aircraft storage system.

Therefore it is an object of the invention to provide a method and apparatus for regulating gas flow that does not experience the exhibited by conventional gas flow regulation methods and apparatuses.

SUMMARY

There is disclosed a gas demand device, comprising a main body, a main body inlet formed in the main body, a device outlet orifice formed in the main body, a vent to atmosphere that is formed in the main body, a timing gas flow path that is formed in the main body and which includes a slave chamber and a secondary slave chamber, a demand gas flow path that is formed in the main body and which includes a primary chamber, a main diaphragm disposed in the secondary slave chamber and which divides the secondary slave chamber into first and second regions, and a slave diaphragm disposed in the slave chamber and which divides the slave chamber into first and second regions. The main body inlet is adapted and configured to be connected to a compressed gas source. The device outlet orifice is adapted and configured to direct a gas to a user for inhalation thereof via a device outlet. The timing gas flow path extends from the main body inlet through the second region of the slave chamber, through the first region of the secondary slave chamber, and to the vent. The demand gas flow path extends from the main body inlet through the primary chamber and to a device outlet via the device outlet orifice. The second region of the secondary slave chamber is in fluid communication with the device outlet via an outlet passage. Open and closed positions of the main diaphragm respectively allows and blocks a flow of gas from the second region of the slave chamber through the timing gas flow path, whose open position allows a flow of gas from the second region of the slave chamber through the timing gas flow path to the vent, the main diaphragm being moved from its closed position to its open position when a vacuum is applied to the device outlet. Open and closed positions of the slave diaphragm respectively allows and blocks a flow of gas from the primary chamber through the demand gas flow path, the slave diaphragm being moved from its closed position to its open position after the second region of the slave chamber has been partially depressurized from a pressure $P_1$ to a pressure $P_2$. The main diaphragm is moved from its open position to its closed position after partial depressurization of the second region of the secondary slave chamber from pressure $P_2$ to a pressure $P_3$ and the slave diaphragm is moved from its open position to its closed position after repressurization of the second region of the slave chamber to a pressure above $P_2$.

There is also disclosed a method of installing the above gas demand device, comprising the steps of fluidly connecting the device outlet orifice to a facemask, nasal mask or nasal cannula and fluidly connecting the main body inlet to a compressed gas cylinder containing an inhalation gas.

There is also disclosed a gas delivery system, comprising the above fluidly connected gas demand device, facemask, nasal mask or nasal cannula, and compressed gas cylinder resulting from the above method of installing.

There is also disclosed a method of using the above gas demand device, comprising the step of providing the above gas demand device, wherein:

the device outlet is fluidly connected to a facemask, nasal mask or nasal cannula that is worn by a user;

the main body inlet is fluidly connected to a compressed gas cylinder containing an inhalation gas and is pressure regulated to a pressure $P_1$;

inhaling while wearing the fluidly connected facemask, nasal mask or nasal cannula causes application of a vacuum to the device outlet orifice, moves the main diaphragm from its closed position to its open position, and allows a flow of the gas through the timing gas flow path;

partial depressurization of the second region of the slave chamber from $P_1$ to a pressure $P_2$ moves the slave diaphragm from its closed position to its open position, and allows a flow of the gas through the demand gas flow path;

further depressurization of the second region of the slave chamber from pressure $P_2$ to a pressure $P_3$ moves the main diaphragm from its open position to its closed position and initiates repressurization of the slave chamber; and partial depressurization of the primary chamber moves the slave diaphragm from its open position to its closed position and initiates repressurization of the primary chamber.

Any one or more of the above device, method of installing, gas delivery system, and method of using may include one or more of the following aspects:

the gas demand device is adapted and configured to be operable in a cycle of first, second, third, fourth, and fifth consecutive phases; at an expiration of the first phase and a commencement of the second phase, the slave chamber diaphragm and main diaphragm are in their closed positions to prevent flows of gas through the demand gas and timing gas flow paths, and pressures in the primary chamber and slave chamber second region are equal to a regulated pressure in the main body inlet; in the second phase, a pressure in the slave chamber outlet orifice is sub-atmospheric because of a demand for gas at the device outlet orifice thereby placing the main diaphragm in its open position while the slave diaphragm remains in its closed position and allowing a flow of gas through the timing gas flow path while preventing a flow of gas through the demand gas flow path, a pressure inside the secondary slave chamber first region decreasing during the second phase; the third phase commencing at an expiration of the second phase when a pressure in the slave chamber second region is decreased below a pressure in the slave chamber first region thereby placing the slave diaphragm to its open position while the main diaphragm remains in its open position and allowing a flow of gas through the timing gas and demand gas flow paths, a pressure inside the slave chamber first region decreasing during the third phase; the fourth phase commencing at an expiration of the third phase when a pressure in the secondary slave chamber first region is decreased below a pressure applied by the spring thereby placing the main diaphragm in its closed position while the slave diaphragm remains in its open position to allow a flow of gas through the demand gas flow path and prevent a flow of gas through the timing gas flow path, a pressure inside the slave chamber second region increasing while the pressure inside the slave chamber first region is decreasing during the fourth phase; the fifth phase commencing at an expiration of the fourth phase when a pressure in the slave chamber second region increases beyond that of the slave chamber first region thereby placing the slave diaphragm in its closed position while the main diaphragm remains in its closed position, pressure within the primary chamber increasing during the fifth phase; and the first phase commencing at an expiration of the fifth phase when pressure in the primary chamber builds to a level equal to the regulated pressure in the main body inlet, the slave and main diaphragms remain closed to prevent flows of gas through the demand gas and timing gas flow paths.

the timing gas flow path does not include the primary chamber and the timing gas is received by a slave chamber inlet orifice which feeds it into the second region of the slave chamber.

the timing gas flow path includes the primary chamber, and alternate passage fluidly communicating between the primary chamber and the second region of the slave chamber, where the second region of the slave chamber is downstream of the primary chamber and the timing gas is received through an inlet orifice of the slave chamber.

the second region of the secondary slave chamber is in fluid communication with the device outlet via an outlet passage and the device outlet orifice of the timing gas flow path and the second region of the secondary slave chamber in fluid communication with the device outlet in parallel.

after repressurization of the slave chamber and primary chamber, flows of the timing gas and demand gas through the timing gas and demand gas flow paths is blocked until the user inhales again while wearing the facemask, nasal mask or nasal cannula.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein:

FIG. 13 is a cross-section view of an alternative of the device of FIG. 6 also taken along line E-E.

DESCRIPTION OF PREFERRED EMBODIMENTS

Figure 1:
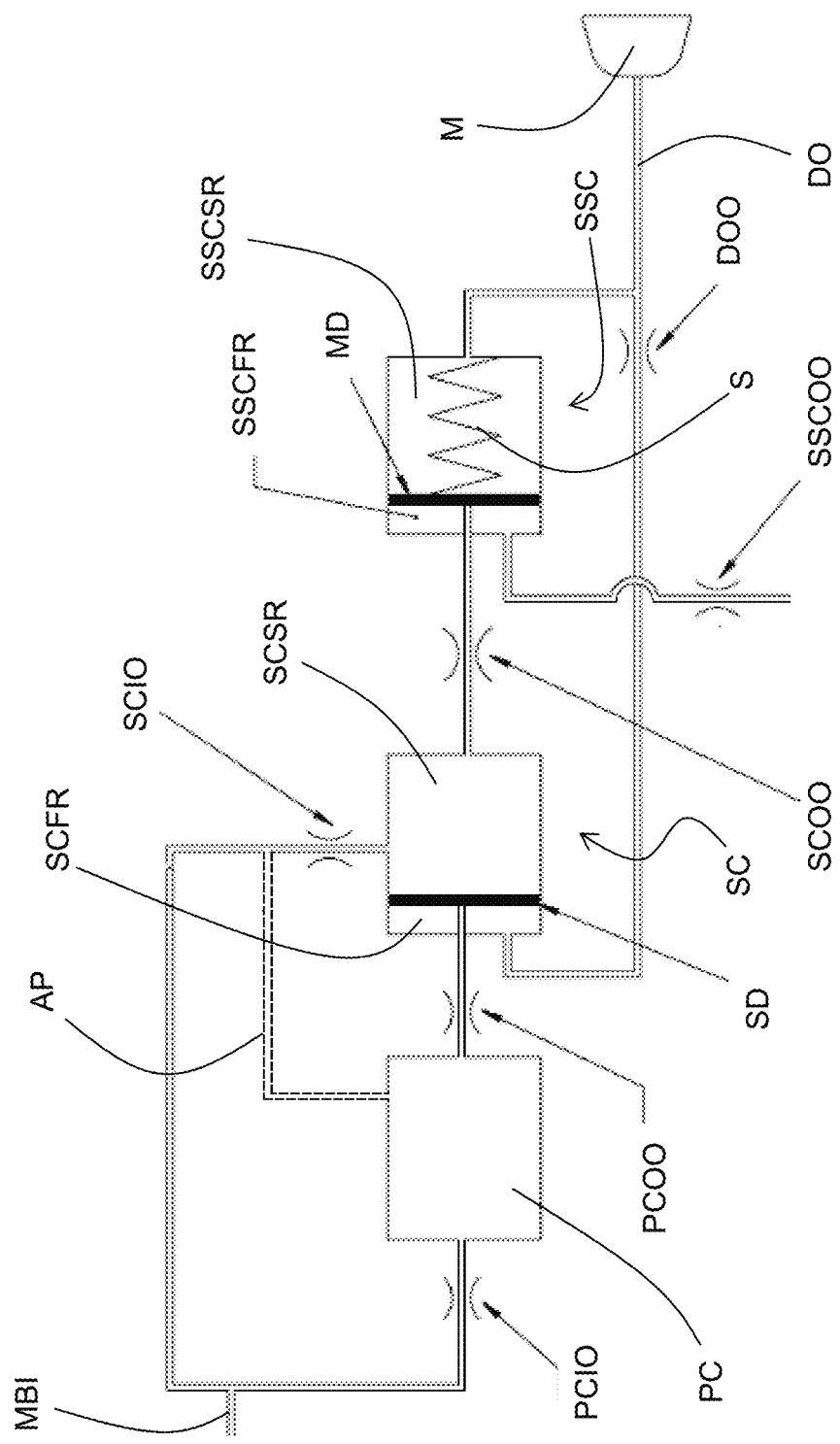
FIG. 1 is a pneumatic schematic visualization of the inventive device at an expiration of a fifth phase of operation and during a first phase of operation.

The inventive gas demand device supplies a gas to a person only upon their inhalation via a facemask, nasal mask or nasal cannula. The gas is delivered in a bolus very quickly upon detection of the start of inhalation. This device may be fitted to various types of gas cylinder valves, whether integrated therewith, configured for standard industry connections to a gas supply, or configured with a proprietary fitting for connection to a gas supply. For use in oxygen therapy, the device is adapted and configured for use with cryogenic oxygen systems, oxygen generators, institution wall oxygen gas outlets, portable oxygen systems, and remotely piped oxygen systems. For use aboard aircraft, the device is adapted and configured for use with oxygen generators (such as chemical oxygen generators or pressure swing adsorption systems) or compressed gas cylinders containing oxygen.

The inventive gas demand device comprises a main body that has a timing gas flow path and a demand gas flow path. The purpose of the timing gas flow path is to provide a flow path from the source of compressed gas, such as a compressed gas cylinder, to atmospheric vent that, over time, will trigger the initiation of a flow of gas along the demand gas flow path from the source of compressed gas to the person inhaling the gas and also trigger the prevention of the flow of gas along the demand gas flow path.

As best illustrated in the pneumatic schematics of FIGS. 1-5, formed in the main body are a primary chamber PC, a slave chamber SC, and a secondary slave chamber SSC. A slave diaphragm SD is disposed within the slave chamber SC and divides it into first SCFR and second regions SCSR on opposite sides of the slave diaphragm SD. A main diaphragm MD is disposed within the secondary slave chamber SSC, is biased to a closed position with a spring, and divides the secondary slave chamber SSC into first and second regions SSCFR, SSCSR on opposite sides of the main diaphragm MD.

The timing gas flow path and the demand gas flow path originate at a main body inlet MBI of the device receiving the compressed gas. The main body inlet MBI is typically provided with standardized threading to receive respective standardized threaded connections of a compressed gas fitting or compressed gas cylinder but may also be provided with a proprietary connection for connection to a compressed gas fitting. The main body inlet MBI includes a pressure regulator section for regulating the pressure of the gas from the compressed gas source to a desired pressure inside the inventive device. Optionally, the device does not include a pressure regulator section within the main body inlet and the pressure of the gas received by the device is instead regulated with a pressure regulator in fluid communication between the device and the source of compressed gas. While the gas of the compressed gas source may be any gas for inhalation by a user of the device, typically the gas is oxygen, oxygen-enriched air, air, a helium-containing gas, or an anesthesia gas.

Downstream of the main body inlet MBI, gas flows in order along the timing gas flow path through a slave chamber inlet orifice SCIO, the second region SCSR of the slave chamber SC, a slave chamber outlet orifice SCOO, and the first region SSCFR of the secondary slave chamber SSC. It is then received by a secondary slave chamber outlet orifice SSCOO and vented to atmosphere therefrom. In an alternate embodiment, instead of proceeding directly between the main body inlet MBI and the slave chamber inlet orifice SCIO, the gas may alternatively flow from the main body inlet MBI, into the primary chamber PC via the primary chamber inlet orifice PCIO, and into the slave chamber inlet orifice SCIO via an alternate passage AP.

On the other hand, downstream of the main body inlet MBI, gas flows in order along the demand gas flow path through a primary chamber inlet orifice PCIO, the primary chamber PC, a primary chamber outlet orifice PCOO, the first region SCFR of the slave chamber SC, a device outlet orifice DOO and a device outlet DO where it is then available for inhalation to the user via a facemask, nasal mask or nasal cannula M.

The gas demand device is adapted and configured for operation in a cycle of five consecutive phases of operation. As will be seen below, when the user commences inhalation, a timed flow of gas through the timing gas flow path is initiated. This event in turn triggers later initiation of a timed flow of gas (and predetermined bolus of gas for inhalation by the user) through the demand gas flow path. This latter event in turn triggers the later closing off of the timing gas flow path. The closing off of the timing gas flow path in turn triggers the later closing off of the demand gas flow path.

The device is operable in five phases.

As best shown in FIG. 1, in concert with orifices SCIO, PCIO, SCOO, PCOO, SSCOO, DOO formed in the timing gas and demand gas flow paths, the slave and main diaphragms SD, MD cooperate to prevent a flow of gas through either of the timing gas and demand gas flow paths during the first phase. No demand for gas via inhalation of the user has yet occurred. Therefore, the pressure in the second region SCSR of the secondary slave chamber is not sub-atmospheric and the main diaphragm MD is biased closed by the spring S. As a result, no gas flows out of the slave chamber outlet orifice SCOO and into the secondary slave chamber outlet orifice SSCOO via the first region SSCFR of the secondary slave chamber SSC. Also, the slave chamber diaphragm SD has been previously forced to its closed position at the expiration of the fourth phase and the commencement of the fifth phase. The pressure in the primary chamber PC and slave chamber SC are at a predetermined pressure P1 equal to the regulated pressure at the main body inlet MBI. Because the pressure is equalized across the slave chamber diaphragm SD, it remains in the closed position.

Figure 2:
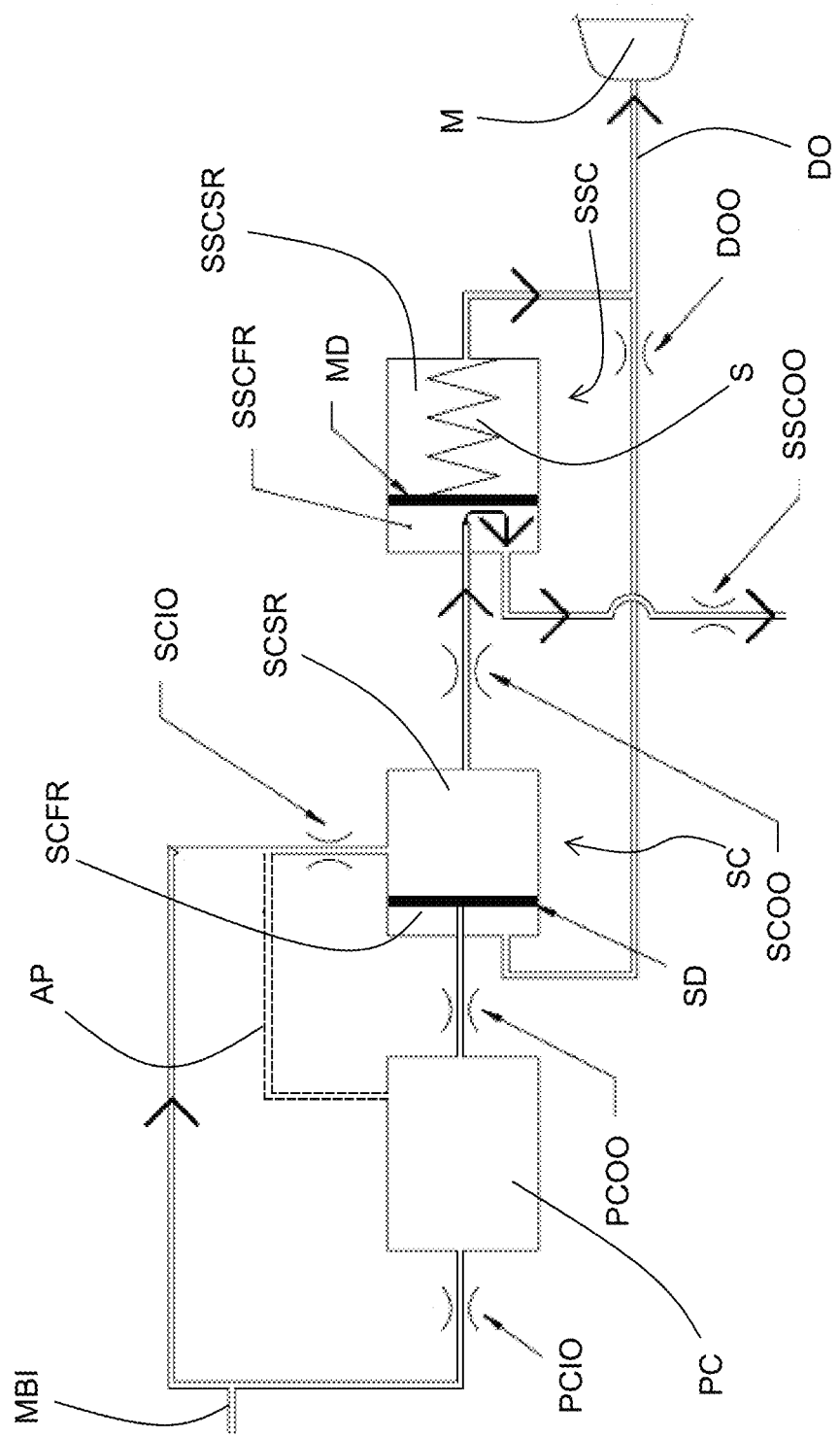
FIG. 2 is a pneumatic schematic visualization of the inventive device during a second phase of operation.

As best shown in FIG. 2, in concert with orifices SCIO, PCIO, SCOO, PCOO, SSCOO, DOO formed in the timing gas and demand gas flow paths, the slave and main diaphragms SD, MD cooperate to allow a flow of gas through the timing gas flow path during a second phase of operation while not allowing a flow of gas through the demand gas flow path. During the second phase, the pressure of the gas in the second region SCSR of the slave chamber SC (as part of the timing gas flow path) SCSR starts at P1 and slowly decreases because it is ultimately vented to atmosphere (from the timing gas flow path) via the secondary slave chamber outlet orifice SSCOO. On the other hand, the pressure of the gas in the first region SCFR of the slave chamber is decreased to a level P2<P1 because a small vacuum is present in the device outlet orifice caused by inhalation by the user. Thus, the pressure of the gas in the second region of the slave chamber SCSR is still higher than the pressure in the first region SCFR of the slave chamber SC (as part of the demand gas flow path). Because of this pressure differential, the slave diaphragm SD remains forced into its closed position where it blocks a flow of gas from the outlet orifice of the primary chamber PCOO into the first region SCFR of the slave chamber SC. Therefore, a flow of gas through the demand gas flow path is prevented. It should be noted, however, that during the second phase, this pressure differential across the slave diaphragm SD decreases because the pressure of the gas in the second region SCSR of the slave chamber SC decreases (by virtue of being vented to atmosphere) while the slight vacuum in the device outlet orifice DOO created by inhalation remains more or less about the same. The second phase expires and the third phase commences when the pressure differential across the slave diaphragm SD is reversed. In other words, the pressure in the second region SCSR of the slave chamber SC is <P2.

Figure 3:
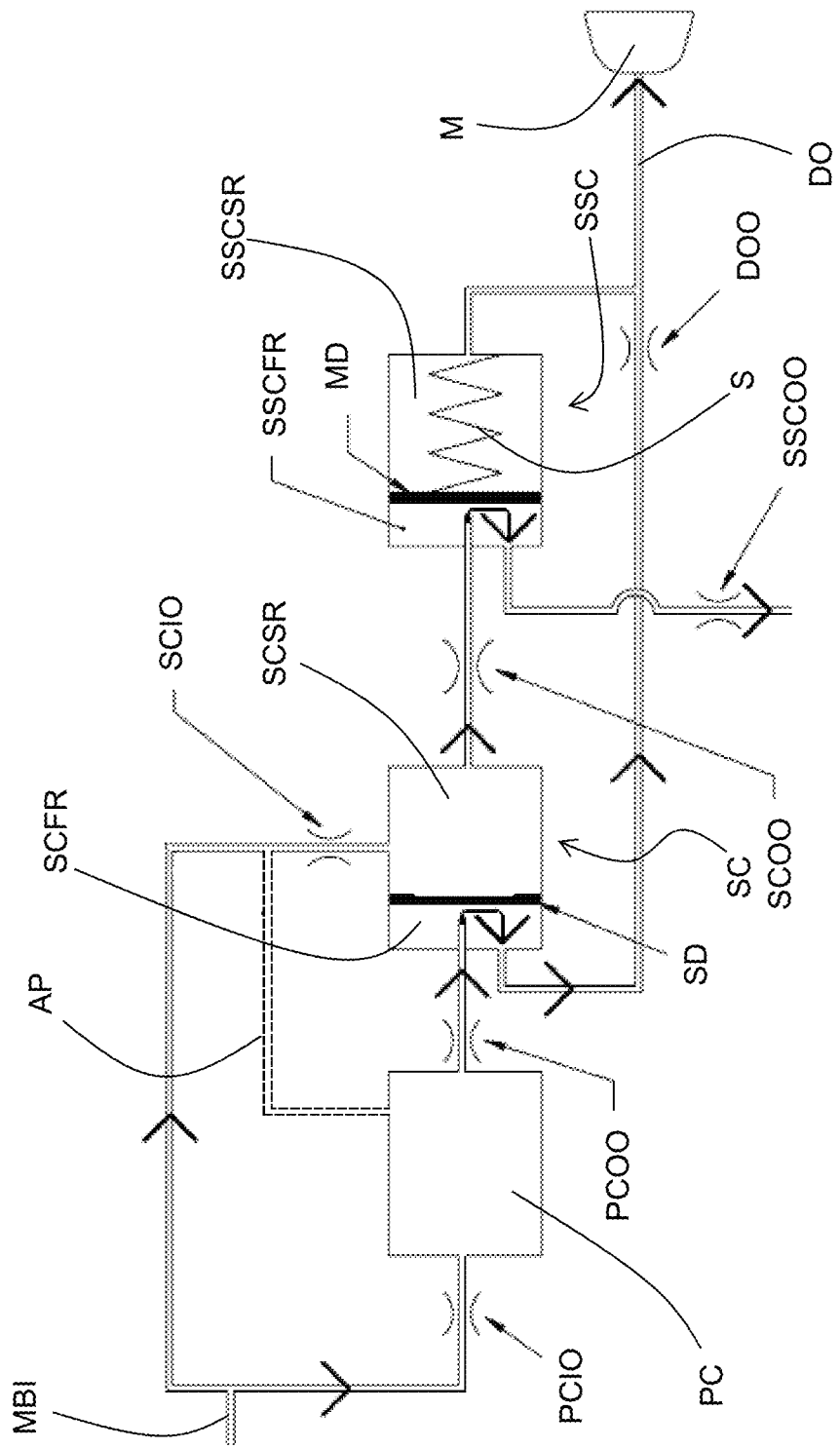
FIG. 3 is a pneumatic schematic visualization of the inventive device during a third phase of operation.

As best shown in FIG. 3, in concert with orifices SCIO, PCIO, SCOO, PCOO, SSCOO, DOO formed in the timing gas and demand gas flow paths, the slave and main diaphragms SD, MD cooperate to allow flows of gas through each of the timing gas and demand gas flow paths during the third phase. During this phase, because the gas is vented to atmosphere from the secondary slave chamber outlet orifice SSCOO, the pressure of the gas in the second region SCSR of the slave chamber SC is now less than the pressure P2 of the gas in the SCFR. As a result of this reversal of pressure differential compared to the second phase, the slave diaphragm SD is forced from its closed position (at the beginning of the third phase) to its open position, thereby allowing a flow of gas from the outlet orifice PCOO of the primary chamber PC, through the first region SCFR of the slave chamber SC and the device outlet DO via the device outlet orifice DOO for inhalation by the user. It should be noted that, during the third phase, the pressure in the first region SSCFR of the secondary slave chamber SSC is decreasing from an initial pressure P2. Since the flow of gas through the timing gas flow path was initiated earlier (i.e., during the first phase) than the flow of gas through the demand gas flow path, the pressure in the slave chamber outlet orifice SCOO and the first region SSCFR of the secondary slave chamber will decrease to a level that is no longer sufficient to overcome the bias supplied by a spring S to the main diaphragm MD. When the pressure in the first region SSCFR of the secondary slave chamber SSC reaches that level, the main diaphragm MD is forced to its closed position, the third phase expires and the fourth phase commences.

Figure 4:
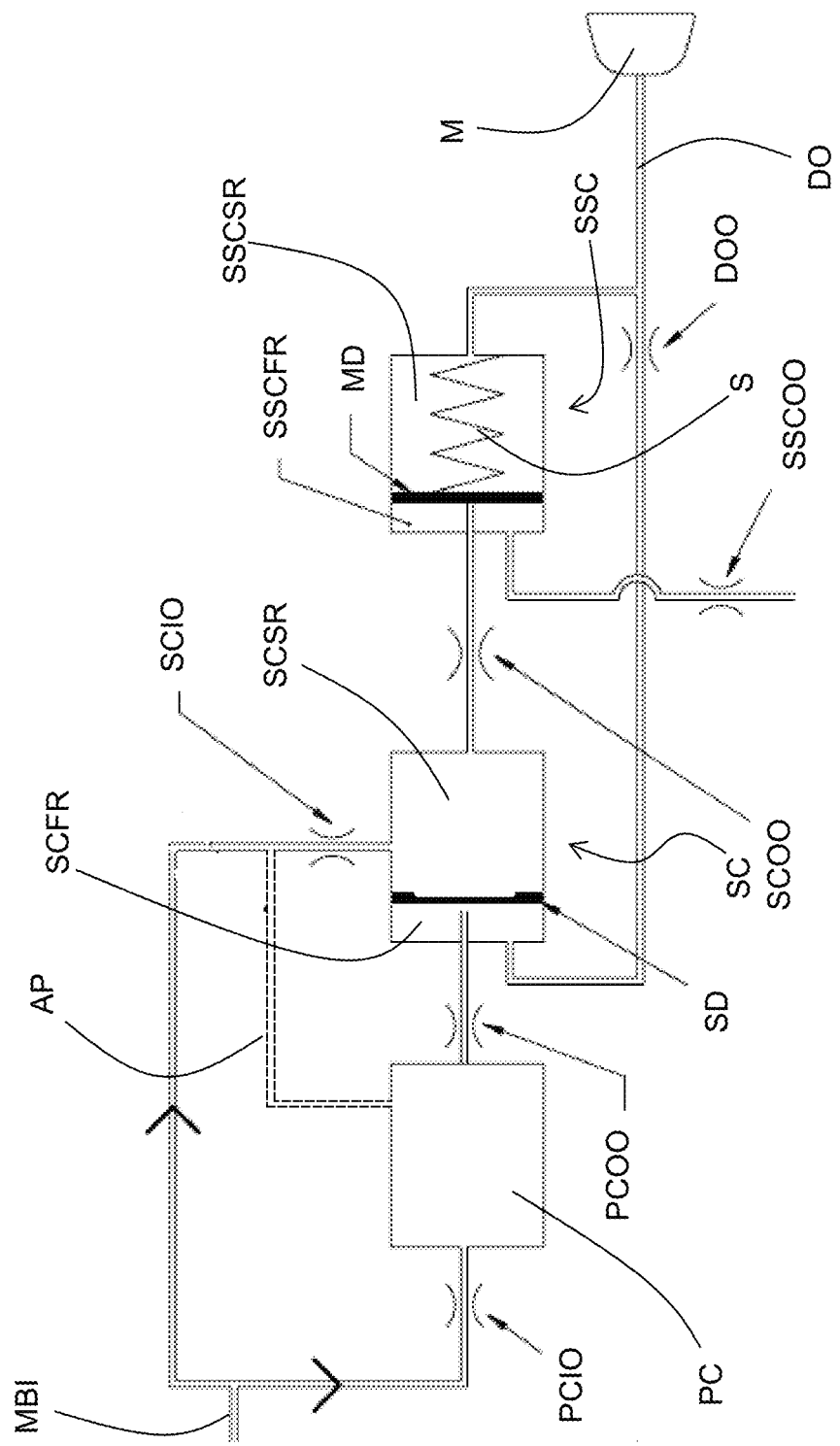
FIG. 4 is a pneumatic schematic visualization of the inventive device during a fourth phase of operation.

As best shown in FIG. 4, in concert with orifices SCIO, PCIO, SCOO, PCOO, SSCOO, DOO formed in the timing gas and demand gas flow paths, the slave and main diaphragms SD, MD cooperate to allow a flow of gas through the demand gas flow path but prevent a flow of gas through the timing gas flow path during the fourth phase. As mentioned above, at the expiration of the third phase, the pressure inside the slave chamber outlet orifice SCOO is no longer sufficient to hold the main diaphragm MD in its open position against the bias supplied by the spring S. Therefore, during the fourth phase there is no gas flow from the slave chamber outlet orifice SCOO through the first region SSCFR of the secondary slave chamber SSC and to vent via the secondary slave chamber outlet orifice SSCOO. Since the flow of gas through the timing gas flow path was initiated earlier (i.e., during the second phase) than the flow of gas through the demand gas flow path, the pressure in the first region SCFR of the slave chamber SC remains higher than that of the second region SCSR. This pressure differential keeps the slave diaphragm SD in its open position. Nevertheless, because the flow of gas through the timing gas flow path has been prevented (as explained before), the pressure in the second region of the slave chamber SC increases during the fourth phase while the pressure in the first region SCFR of the slave chamber SC decreases. When the pressure in the second region SCSR of the slave chamber SC rises above that of the first region SCFR, the slave diaphragm SD is forced to its closed position, the fourth phase expires and the fifth phase commences.

Figure 5:
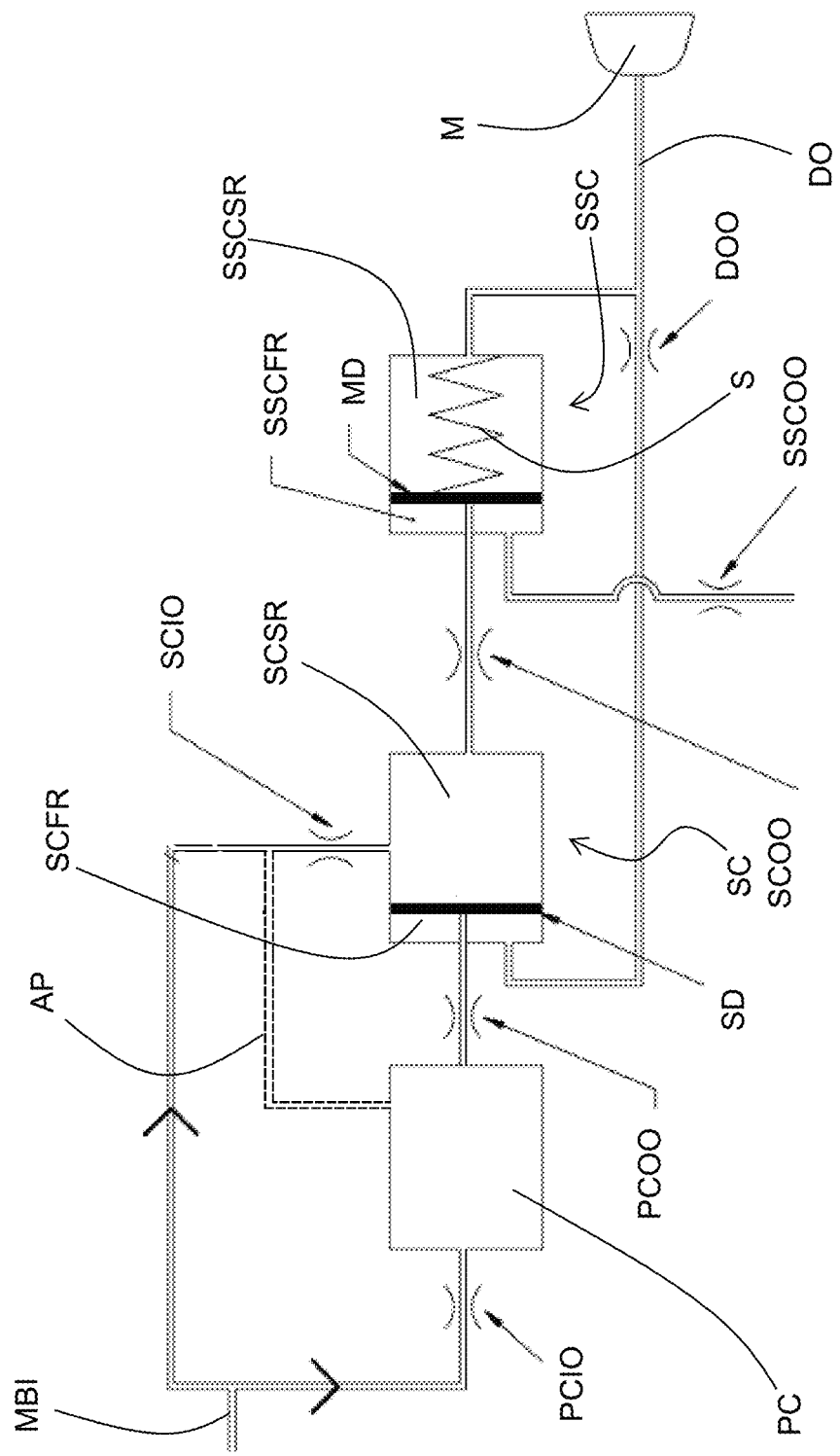
FIG. 5 is a pneumatic schematic visualization of the inventive device during the fifth phase of operation.

As best shown in FIG. 5, in concert with orifices SCIO, PCIO, SCOO, PCOO, SSCOO, DOO formed in the timing gas and demand gas flow paths, the slave and main diaphragms SD, MD cooperate to prevent flows of gas through the demand gas and timing gas flow paths during the fifth phase. In contrast to the first phase, there is a pressure differential across the slave diaphragm SD. Once pressure equalization of the primary chamber PC and second region SCSR of the slave chamber SC with the regulated pressure of the main body inlet is reached, the fifth phase expires and the first phase commences unless, of course, the user inhales gas precisely at the expiration of the fifth phase, in which case operation advances directly to the second phase. Typically, the user does not perform such a simultaneous inhalation, and the first, static phase is reached until inhalation begins.

A particular embodiment of the inventive device will now be described with reference to FIGS. 6-13.

A main body 1 of the inventive device includes a main body inlet 10 that is adapted and configured to receiving gas from a source of compressed gas, such as a compressed gas cylinder or gas fitting that itself is in fluid communication with a compressed gas cylinder or similar gas storage device. The inlet 10 includes a pressure regulator section 15 which regulates the pressure of the gas received from the source of compressed gas down the desired operating pressure P1. Optionally, the inlet 10 does not include a pressure regulator section 15 and the pressure is instead regulated with a pressure regulator disposed in fluid communication between the compressed gas source and the inlet 10 in which case the regulated pressure is still P1. While the inlet 10 may be permanently mounted to the outlet of a compressed gas cylinder, typically the inlet 10 is provided with threading that is sized to receive and frictionally engage with corresponding standardized threading on compressed gas cylinder in order to allow an empty cylinder to be conveniently changed out with a full cylinder. The types of gases delivered by the inventive gas demand device are not limited. Typically, the gas is oxygen, oxygen-enriched air, air, helium-containing gas, or anesthesia gases.

The main body 1 also includes a device outlet orifice 11 that is adapted and configured to direct inhalation gas to a facemask, nasal mask or nasal cannula (not illustrated) that is worn/used by the user. The type of user is not limited. One typical type of user is a patient receiving inhaled gas therapy, such as oxygen therapy. Another typically type of user a member of the crew of an aircraft or a passenger of an aircraft, especially in low oxygen and/or low pressure conditions.

Figure 10:
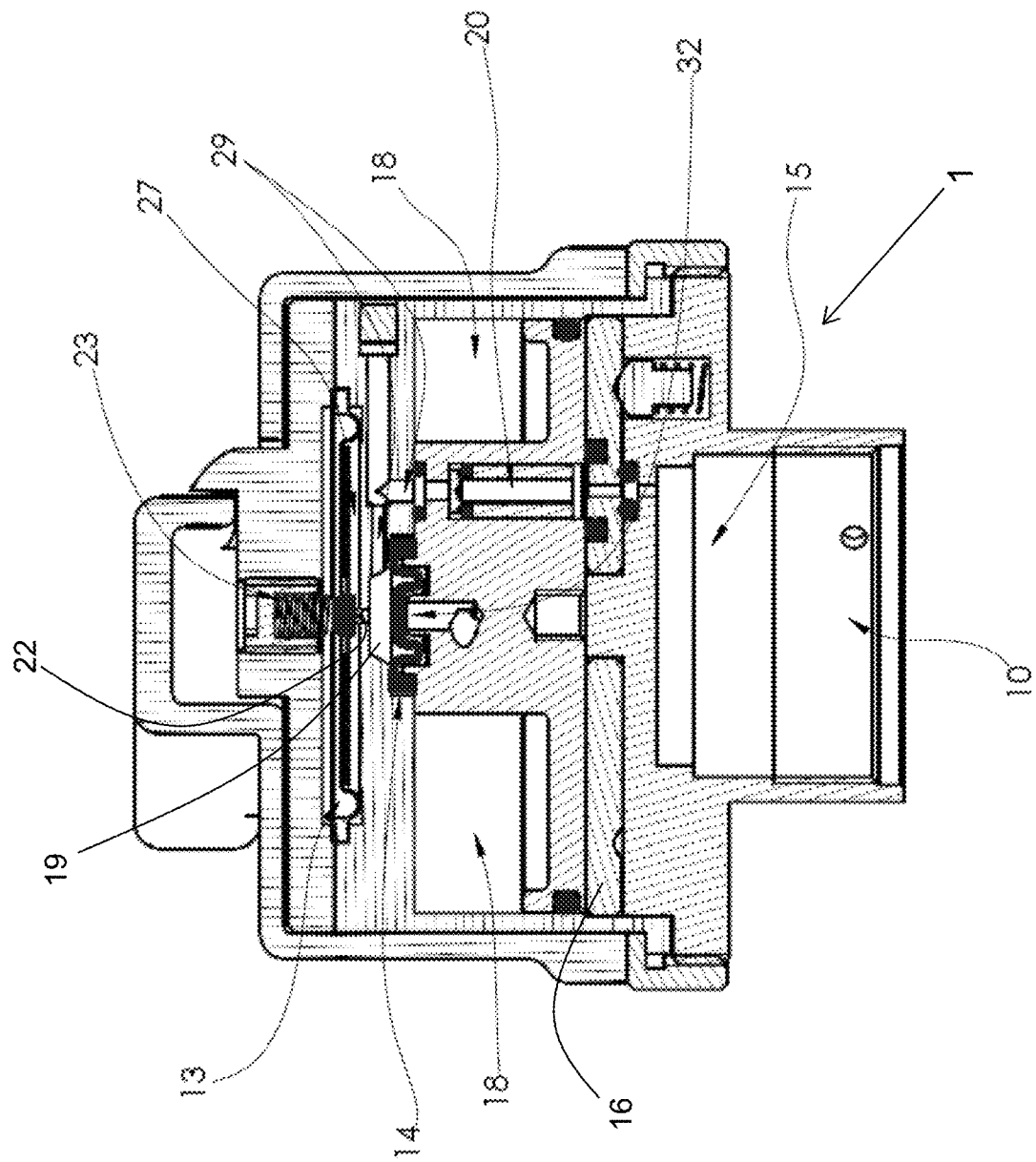
FIG. 10 is a cross-section view of the device of FIG. 6 taken along line D-D.
Figure 11:
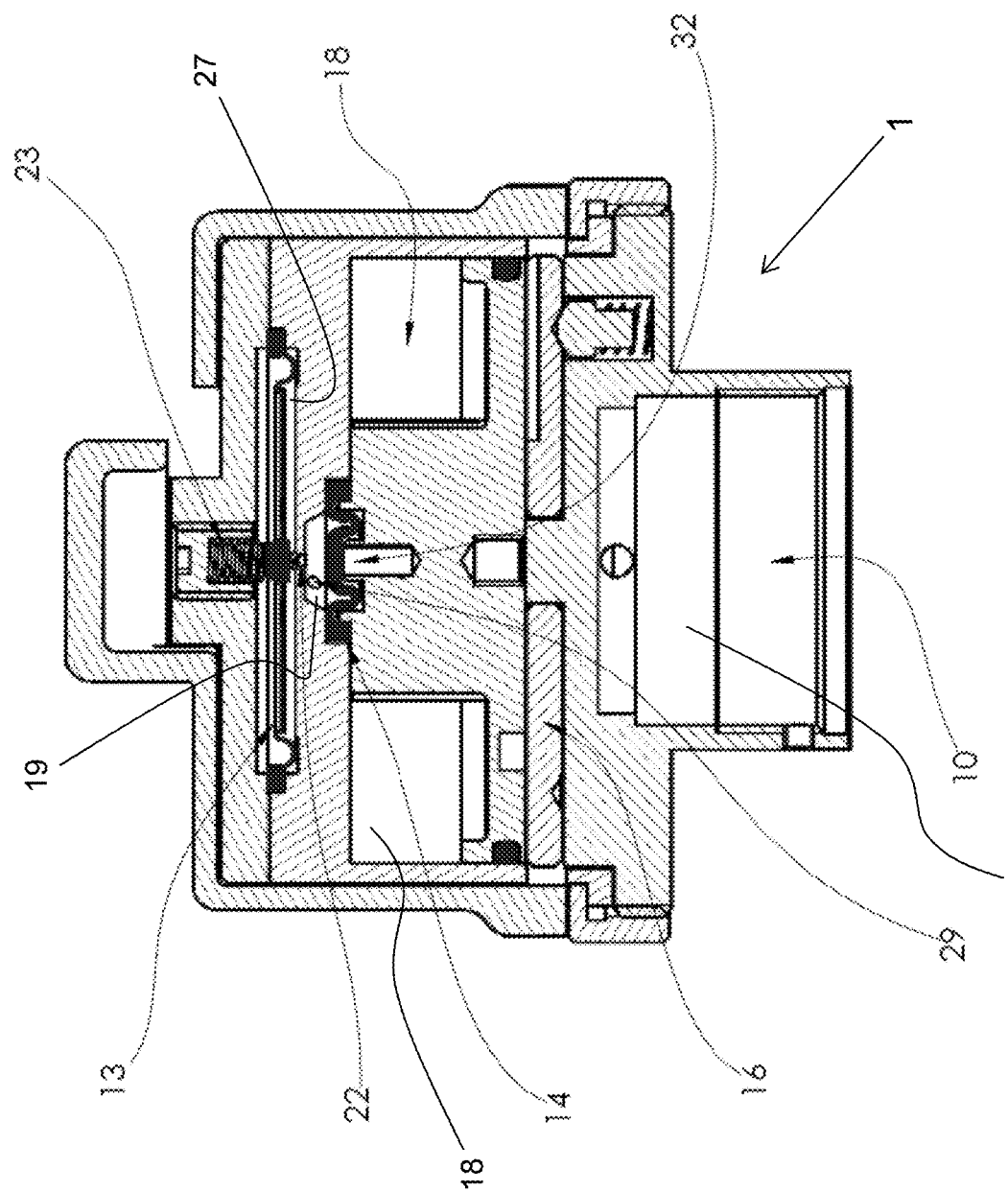
FIG. 11 is a cross-section view of the device of FIG. 6 taken along line B-B.
Figure 12:
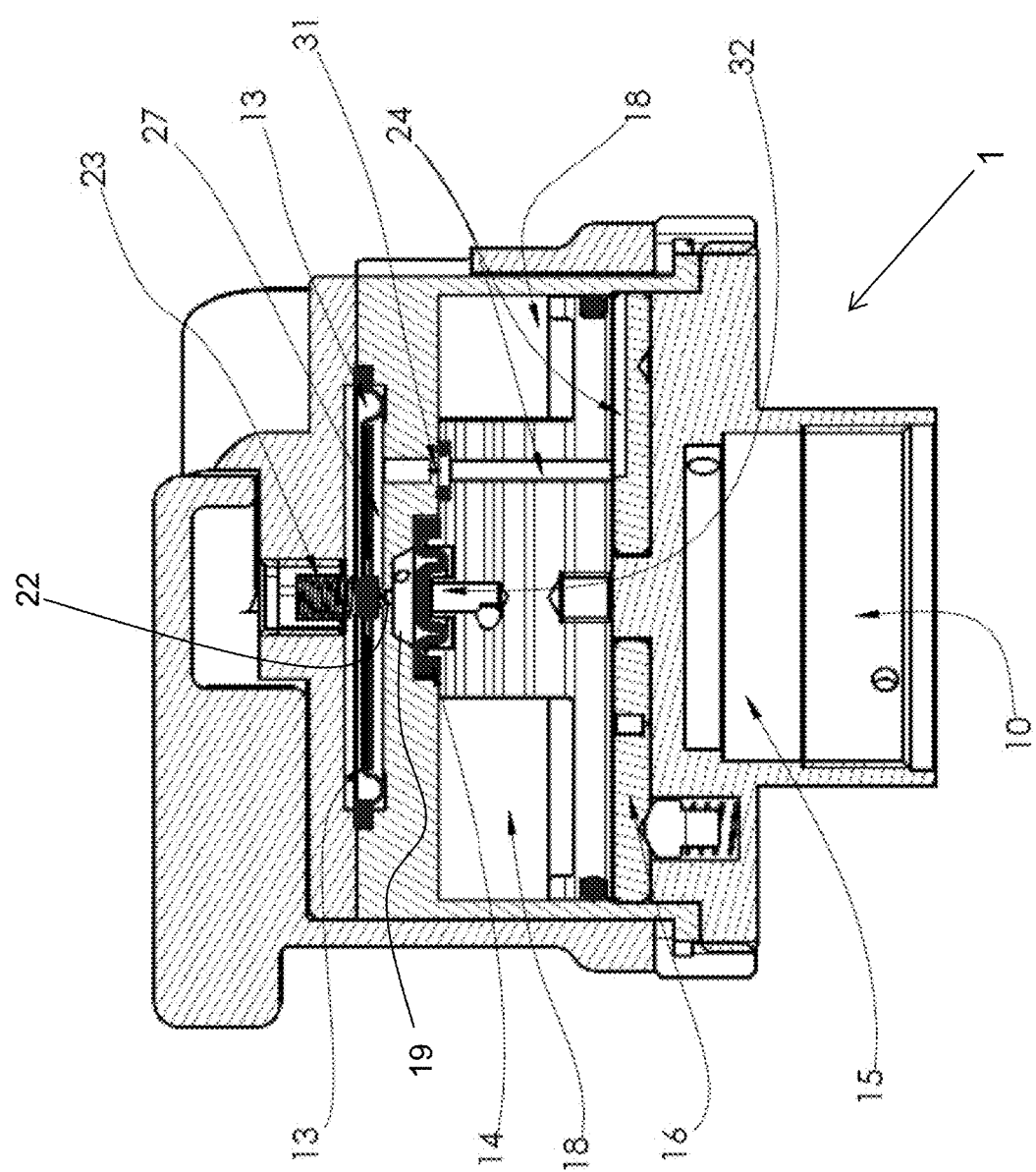
FIG. 12 is a cross-section view of the device of FIG. 6 taken along line C-C.

The timing gas flow path originates at the main body inlet 10. A slave diaphragm 14 divides a slave chamber 19 into a first region below the slave diaphragm 14 in FIGS. 9-13 and a second region above the slave diaphragm 14 in FIGS. 9-13. As shown in FIG. 10, the second region of the slave chamber 19 is supplied with the gas via passage 29 and fixed orifice 20 directly from inlet 10.

Figure 6:
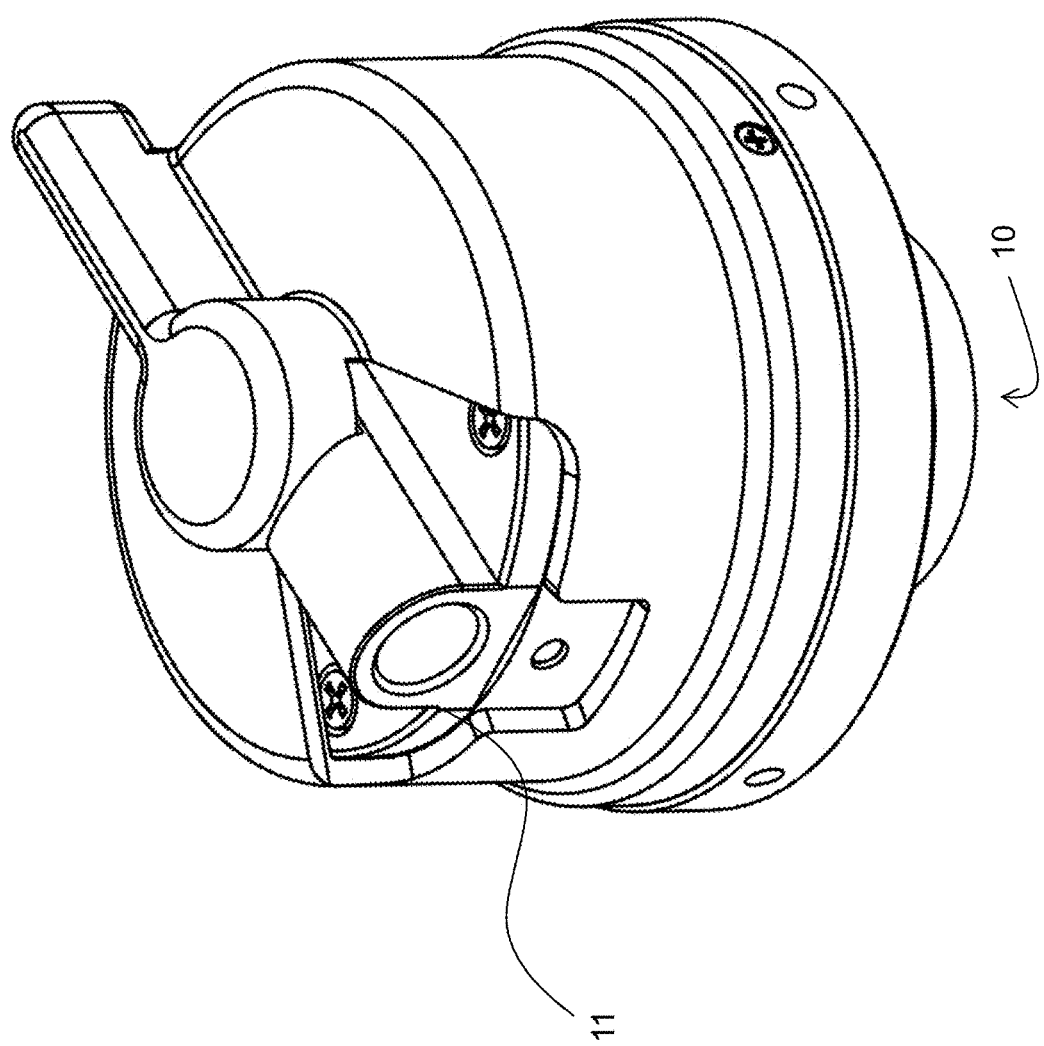
FIG. 6 is a perspective view of an embodiment of the inventive device.
Figure 7:
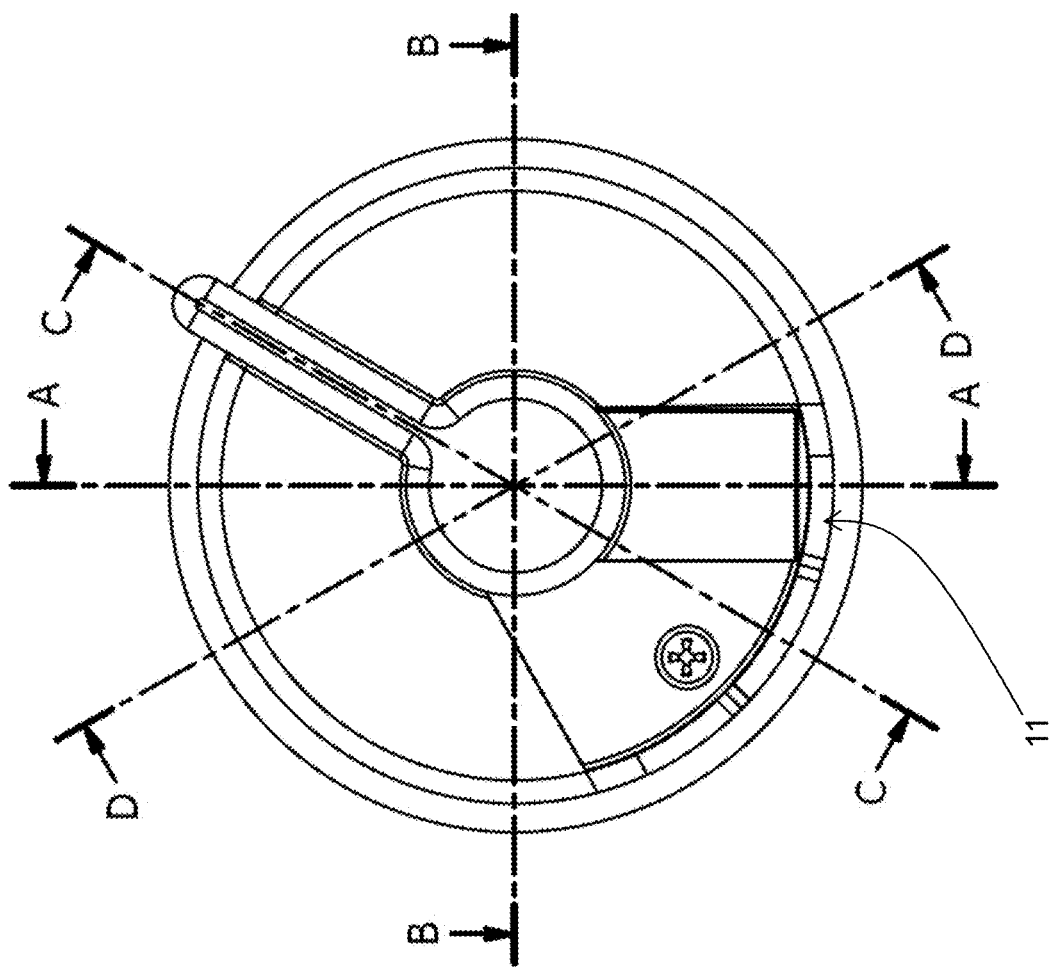
FIG. 7 is a top plan view of the device of FIG. 6.
Figure 8:
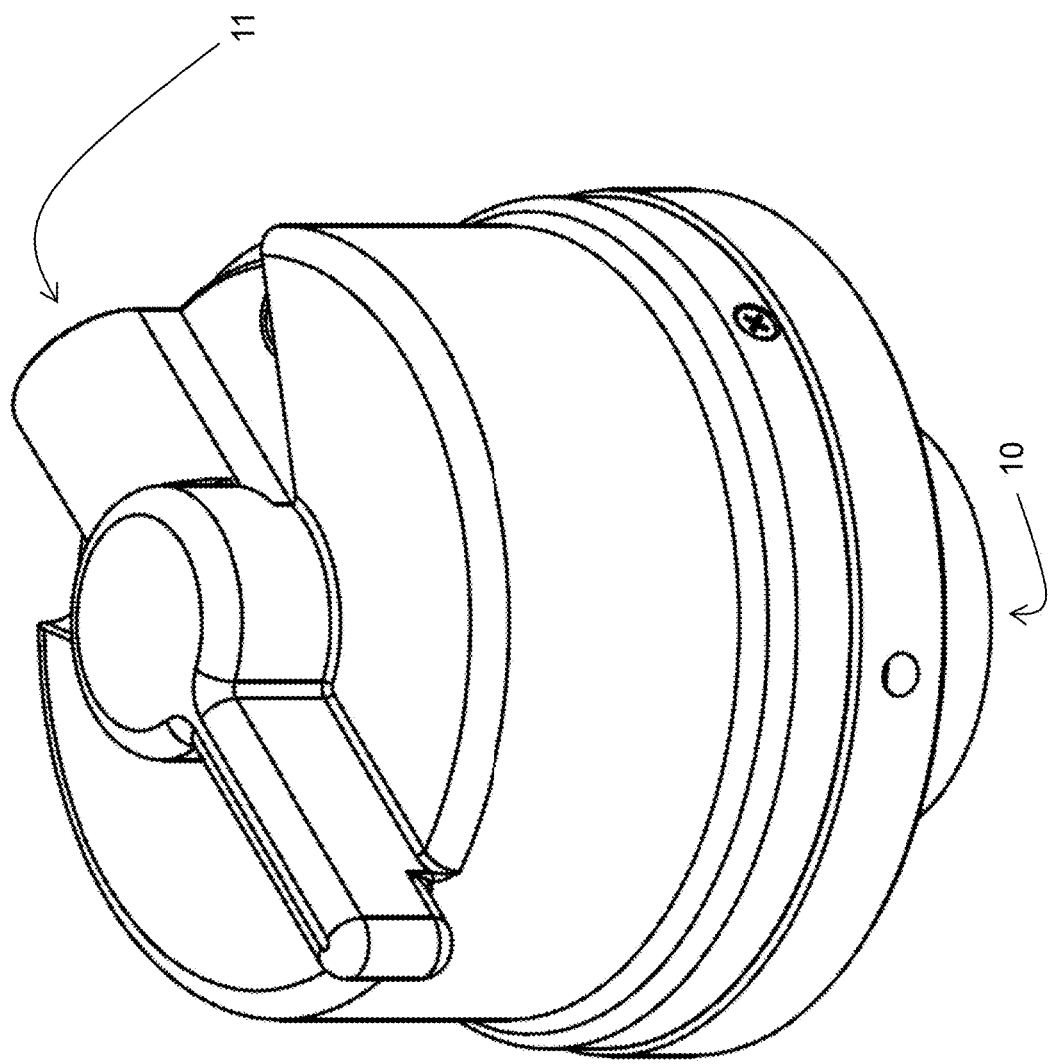
FIG. 8 is a perspective view of an embodiment of the inventive device of FIG. 6 taken at an angle to the viewpoint of FIG. 6.
Figure 9:
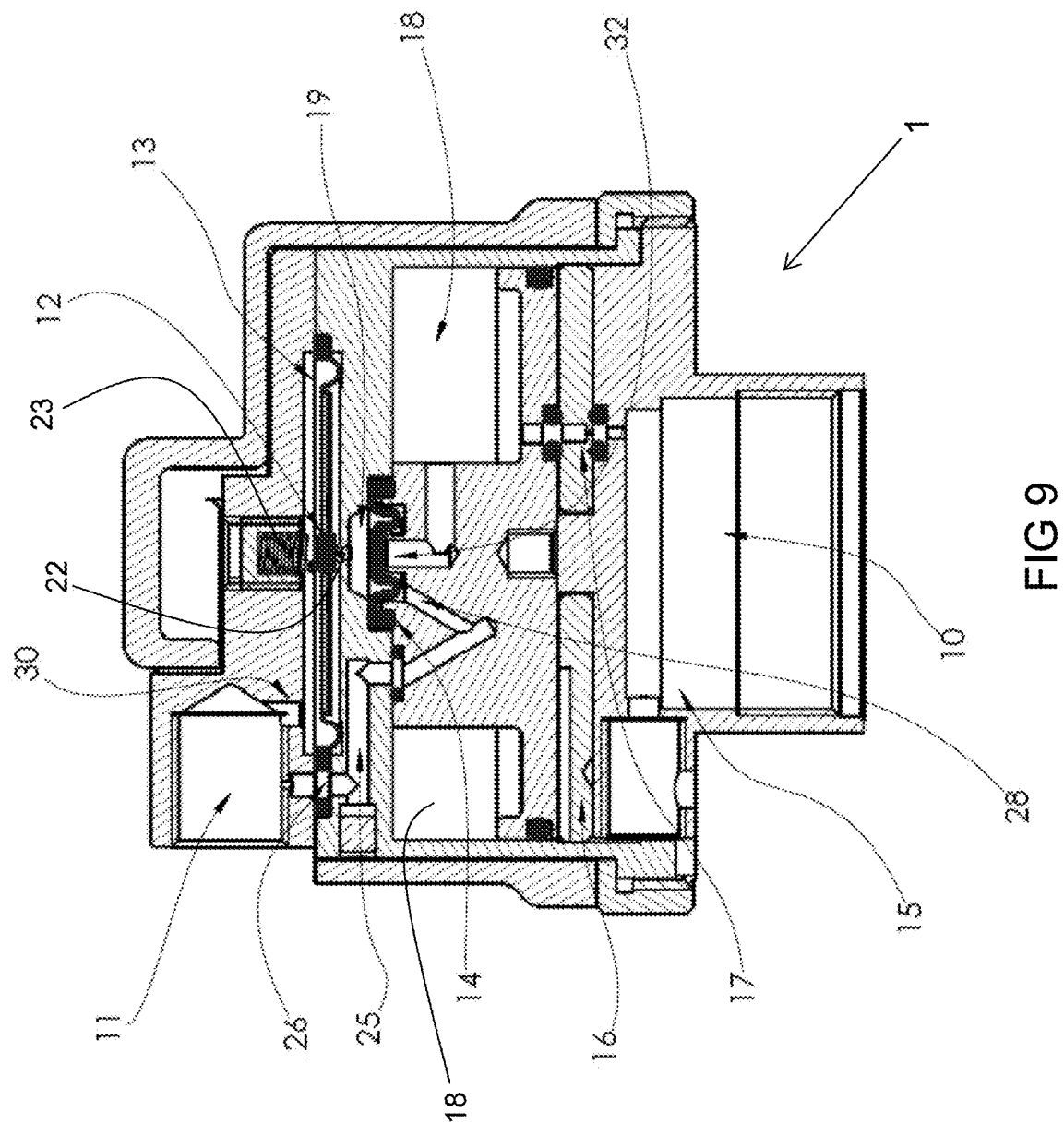
FIG. 9 is a cross-section view of the device of FIG. 6 taken along line A-A.

An alternative embodiment to that of FIG. 6 is partially illustrated in FIG. 13. In the alternative embodiment of FIG. 13, all of the features and views of the embodiment of FIGS. 6-9 and 11-12 are the same except for the lack of a fixed orifice 20 and passage 29 and for the way that the second region of the slave chamber 19 is supplied with gas from inlet 10. With this in mind, the alternative embodiment illustrated in FIG. 13 is a cross-sectional view taken along line D-D where the second region of the slave chamber 19 is instead supplied with gas from the primary chamber via a fixed orifice 21.

A main diaphragm 13 divides a secondary slave chamber 27 into a first region below the main diaphragm 13 and a second region above the main diaphragm 13 and is biased in its closed position by a spring 23. A slave chamber outlet orifice 22 fluidly communicating between the second region of the slave chamber 19 and the first region of the secondary slave chamber 27 is blocked by the main diaphragm 13 in its closed position. When the user initiates inhalation, a slight vacuum will be created at the device outlet orifice 11. Because the second region of the secondary slave chamber 27 is in fluid communication with the device outlet orifice 11 via outlet passage 30, a slight vacuum will also be caused in the second region of the secondary slave chamber 27 upon inhalation by the user. This slight vacuum overcomes the bias of spring 23 so as to move the main diaphragm 13 to its open position. When the main diaphragm 13 is moved to its open position, the gas flows out of the second region of the slave chamber 19, through the slave chamber outlet orifice 12, through the first region of the secondary slave chamber 27, through a secondary slave chamber outlet orifice 31, and vented to atmosphere from port 24. Thus, flow through the timing gas flow path is initiated.

The demand gas flow path also originates from the main body inlet 10. The gas passes through a fixed inlet orifice 17 and into primary chamber 18. Alternatively, the gas instead passes through one of a set of orifices formed in a selectable orifice disk 16 where each of these alternative orifices is formed at a same radial distance from a center of disk 16. In this alternative arrangement, the disk 16 may be rotated in order to place the appropriate sized and desired orifice in fluid communication between the inlet 10 and the primary chamber 18. It should be noted that the fixed inlet orifice 17 or the selectable orifice in selectable orifice disk 16 constitutes the above-described primary chamber inlet orifice. In its closed position, the slave diaphragm 14 closes primary chamber outlet orifice 28.

We will now describe how the slave diaphragm 14 is opened and the flow of gas through the demand gas flow path is commenced.

The slave diaphragm 14 is normally biased closed. Those of ordinary skill in the art will understand this to mean that the slave diaphragm 14 is in its closed position when the pressure of the second region of the slave chamber 19 is equal or greater than the pressure of the first region of the slave chamber 19. They will further understand that the slave diaphragm 14 is in its open position when the pressure of the second region of the slave chamber 19 is less than the pressure of the region of the slave chamber 19. During the second phase, because the gas in the timing gas flow path is vented to atmosphere, the pressure inside the second region of the slave chamber 19 decreases from an initial pressure $P1$ after initiation of the flow through the timing gas flow path. At the beginning of the second phase, the primary chamber outlet orifice 32 is at a pressure $P2$. This pressure $P2$ is less than $P1$ because a slight vacuum caused by inhalation of the user decreases $P1$ to a small degree. In other words, $P1$–the vacuum=$P2$. When the pressure inside the second region of the slave chamber 19 decreases below $P2$, the second phase expires, the third phase commences, and the slave diaphragm 14 is moved to its open position. When the slave diaphragm 14 is in its open position, gas is allowed to flow from the primary chamber 18 through the primary chamber outlet orifice 32, into the slave chamber first region, through orifice 28 and the primary chamber passage 25, through outlet orifice 26, and ultimately to the user via device outlet orifice 11.

As a result of inhalation by the user and movement of the main diaphragm 13 to its open position, a timer mechanism is started. The timer starts at $t_0$ when the first phase expires, the second phase commences and flow of the gas through the timing gas flow path is initiated. The timer reaches $t_1$ when the second phase expires, the third phase commences, and flow of the gas through the demand gas flow path is commenced by movement of the slave diaphragm 14 to its open position. The timer reaches $t_2$ when the third phase expires, the fourth phase commences, the flow of gas through the timing gas flow path is blocked by the movement of the main diaphragm 13 to its closed position, and the flow of gas through the demand gas flow path continues. The timer reaches $t_3$ when the fourth phase expires, the fifth phase commences, and the flow of gas through the demand gas flow path is blocked by movement of the slave diaphragm 14 to its closed position. The timer is reset to $t_0$ when the fifth phase expires, the first phase commences and the primary chamber 18 and the second region of the slave chamber 19 reach $P1$. In comparison to many convention gas demand devices, this timer mechanism allows the primary chamber 18 to release a bolus of gas to the user regardless of any inherent back pressure on the main diaphragm via passage 30.

The cross-sectional dimensions of the orifice 28 and the orifice 26 work in series to control the peak gas flow to the device outlet orifice 11. This prevents the gas flow from exceeding the user's inspiratory flow as well as minimizes any inherent back pressure applied onto the main diaphragm 13 from the outlet flow.

By controlling the gas flow into the primary chamber 18 via the selectable inlet orifice disc 16 or via the fixed inlet orifice 17, the inventive device controls the gas volume of each cycle or breath via device outlet orifice 11. This gas volume is dependent upon the frequency of each cycle and the flow rate of gas through the demand gas flow path. Therefore, if the frequency of each cycle can be increased or decreased, for a given flow rate of gas through the demand gas flow path, the total volume of gas per minute delivered to the user per minute (considered over the entire cycle) may be correspondingly increased or decreased. This may be conveniently done through selection of the desired orifice in the selectable inlet orifice disc 16 the fixed inlet orifice. In other words, the disc 16 may be rotated in order to select an appropriately sized orifice that will yield the desired the total volume of gas per minute delivered to the user (considered over the entire cycle).

While the inventive gas demand device may be used for anything requiring a controlled flow of gas delivered in boluses in a cyclical fashion, the inventive gas demand device is typically used by either a patient in gas therapy, such as oxygen therapy with oxygen, oxygen-enriched gas, or compressed air, or by the crew or passengers of an aircraft during low oxygen and/or pressure conditions.

Whether used by a patient for gas therapy or by aircraft crew in low oxygen and/or low pressure environments, in comparison to conventional gas demand devices, the inventive device has several advantages.

The inventive device reduces the required size and/or weight of an oxygen supply vessel (such as a compressed gas cylinder) and/or increases the time of use in between successive refilling or replacement of the vessel. Decreased size and/or weight are important in the gas therapy context for patients who may experience, muscular weakness, lack of muscle tone, and/or lack of stamina. Decreased size and/or weight will also ordinarily result in decreased costs for the manufacturer, insurer, and/or patient.

Decreased size and/or weight are also important in the aerospace context. Aerospace oxygen systems are typically only used in the rare occurrence of a cabin depressurization in the worst case or to provide first aid to an ill passenger. Regardless, every flight must care enough oxygen supply to meet the worst case scenario. Consequently, the weight of these systems on board consumes fuel, reduces payload and range and increases operating costs. Current systems for on-board oxygen provide continuous flow oxygen. Continuous flow limits the duration of time during which the oxygen is supplied. Continuous flow also requires the maximum size supply vessel that the storage space. When an aircraft is used with a same continuous flow system on both short-distance and long-distance flights, the oxygen requirements for the long-distance flight will control. Thus, long-distance flights will a bulkier and/or heavier continuous flow system that decreases fuel consumption. While short-distance flights may utilize a less bulky and/or less heavy continuous flow system, such a system will limit the range of the aircraft on a subsequent flight unless the system is swapped out with a more bulky and/or heavier continuous flow system. By using the inventive gas demand device, the weight can be reduced. Therefore, the aircraft range and/or payload may be increased and fuel consumption decreased. Indeed, in comparison to some conventional systems, the inventive device can reduce the amount of oxygen required on the typical aircraft by as much as 75%. The weight reduction achievable by the inventive device can also improve safety and maintenance costs as well enabling the use of compressed gas cylinders rather than chemical oxygen generators.

Many conventional devices are electrically powered with a battery and may suffer from power failures, voltage errors and are generally heavier due to the weight of the battery. In contrast, the inventive device functions pneumatically and does not require any electrical power or batteries.

Many conventional devices include features which are freely movable within the device and which may be impacted by the relative position of the device by the force of gravity. For example, some conventional devices may include a ball-type check valve intended to reduce the amount of back pressure created when a pulse of oxygen exits the device and prematurely forces a diaphragm closed. This type of valve is a positional valve that only functions properly when the device is in an orientation where gravity keeps the check valve ball away from its seat. Should the device be inverted the check valve ball will fall to its seat and occlude the passage to the diaphragm, the device may not function since the check valve ball can remain occluded if the inspiration from the user is not great enough to lift the ball from its seat. The amount of negative pressure (<−1.00 cm $H_2O$) typically created by the user at an outlet of such device would most likely not be enough to lift the check valve ball off its seat. In contrast, operation of the inventive device does not depend upon how it is positioned or oriented. In other words, the main diaphragm will not be prematurely closed and operation will not change if the position of the inventive device is changed.

The inventive design is small and easy to use and can be configured and adapted to several modalities such as compressed gas high pressure cylinders, cryogenic oxygen systems, oxygen generators, institution wall oxygen gas outlets, portable oxygen systems and remotely piped oxygen systems.

While some conventional home healthcare gas demand systems have been tried in the commercial aviation market with limited acceptance and success, most were not durable enough for the rigors of the commercial aviation market or provide inadequate interface with the aircraft storage system. The inventive device has been designed with the commercial aviation market in mind in order to overcome the problems experienced by many conventional systems as well as for the healthcare market so as to improve upon current gas demand systems for the healthcare market.

Conventional continuous flow compressed gas systems have a limited use time (for inhalation by the user) that is based upon the volume and pressure of the gas cylinder. Put quite simply, the use time is determined by dividing the mass of gas in the cylinder by the flow rate. In contrast, for the same mass of gas in the gas cylinder, the inventive device extends the use time (for inhalation by the user) because it does not use a continuous flow.

Many conventional gas demand devices tend to be complicated, do not control the volume of gas delivered over time, and do not provide the desired pulse bolus flow curve (i.e., a relatively high peak flow for a short duration) that is best for the person using the device. On the other hand, the inventive device provides the desired bolus flow curve.

Some conventional devices deliver multiple pulses in rapid succession creating a saw tooth gas flow pattern that is depend on constant inhalation and does not control the flow over time. In contrast, the inventive device supplies a bolus of gas upon user demand (i.e., inhalation by the user). Thus, it does not deliver another bolus of gas unless it is demanded by the user.

In comparison to many conventional devices, the inventive device exhibits increased reliability, performance, and ease of use, and a decreased rate of failure caused by uncontrolled user interfaces and real world user conditions.

Most conventional devices depend upon either a back pressure from the gas delivery line or back pressure at an outlet of the device in order to close a main diaphragm and reset its pneumatic circuit. The dependence of a back pressure for closing the main diaphragm is because the last orifice upstream of the outlet is located downstream of a fluidic passage to the diaphragm in question. This particular arrangement will result in a varying back pressure upon the diaphragm; consequently, cause an inconsistent volume per minute delivery. In contrast, the combination of the primary chamber outlet orifice, the slave chamber inlet orifice, the slave chamber, the slave chamber outlet orifice, the secondary slave chamber, the slave chamber outlet orifice, and the outlet orifice of the inventive device work together create a timing circuit that is independent of any back pressure exerted onto the main diaphragm. The main diaphragm of the inventive device resets itself based upon the pneumatic timing circuit and the bias of the spring.

Upon opening of the main diaphragm a secondary slave chamber is created. This secondary slave chamber adds to the timing circuit to ensure the main diaphragm followed by the slave diaphragm does not close before the primary chamber empties. This is important to ensure any back pressure on the main diaphragm does not affect the timing and the minute volume is consistent across typical range of breath rates.

An ongoing challenge for most conventional pneumatic demand devices is the ability to be sensitive enough for the person with slow shallow breaths to trigger the device without the device being over sensitive to variations in the gas inlet pressure resulting in the device to self-cycle (auto-pulse). Overly complicated designs exacerbate this sensitivity problem since they magnify the amplitude of any pressure deviations from the specified regulated pressure. In contrast, the design of the pneumatic circuit of the inventive device is simplified, so the amplification of pressure-sensitivity experienced by many conventional devices is significantly dampened in the inventive device. The simplified design of the pneumatic circuit also increases the ease of manufacturing, reduces component count and improves performance. To put a finer point on this assertion, the geometry of the components that make the primary chamber, slave chamber, secondary slave chamber and the orifices in the inventive device are designed to reduce the quantity of components and the cost of the components for manufacturing the device. For example, the device of U.S. Pat. No. 7,089,938 may use as many as 22 components making up the pneumatic circuit while the inventive device may use as few as 15 components.

In the alternative embodiment where gas is supplied directly from the primary chamber to the slave diaphragm inlet orifice, it is important to note that this results in only one supply passage from the gas source in which the flow rate to the second region of the slave chamber is controlled by the dimensions of the slave chamber inlet orifice. In contrast, many conventional devices require two passages to supply the chamber (that is equivalent to the primary chamber of the inventive device) from the gas source. Because only one passage is used in the inventive device, component design is simplified, the amount of overall components is reduced, and performance is improved by controlling the flow rate thru the slave chamber inlet orifice. Because the flow through the slave chamber inlet orifice to the slave chamber is in direct proportion to the pressure in the primary chamber, the time required for the emptying of the primary chamber during each cycle (pulse) is optimized. In other words, the alternative arrangement ensures enough time for the primary chamber to empty, thereby achieving a more consistent volume per minute delivery.

LEGEND main body 1
main body inlet 10
device outlet orifice 11
main diaphragm 13
slave diaphragm 14
pressure regulator section 15
selectable orifice disk 16
fixed orifice 17
primary chamber 18
a slave chamber 19
fixed orifice 20
fixed orifice 21.
slave chamber outlet orifice 22
spring 23
port 24
primary chamber passage 25
outlet orifice 26
a secondary slave chamber 27
primary chamber outlet orifice 28.
passage 29
outlet passage 30
secondary slave chamber outlet orifice 31
primary chamber outlet orifice 32

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within the range.

All references identified herein are each hereby incorporated by reference into this application in their entireties, as well as for the specific information for which each is cited.

What is claimed is:

1. A gas demand device, comprising a main body, a main body inlet formed in the main body, a device outlet orifice formed in the main body, a vent to atmosphere that is formed in the main body, a timing gas flow path that is formed in the main body and which includes a slave chamber and a secondary slave chamber, a demand gas flow path that is formed in the main body and which includes a primary chamber, a primary chamber inlet orifice that comprises a set of orifices formed in a selectable orifice disk formed at a same radial distance from a center of the selectable orifice disk and that may be rotated in order to place a selected one of the set of orifices in fluid communication between the main body inlet and the primary chamber, a main diaphragm disposed in the secondary slave chamber and which divides the secondary slave chamber into first and second regions, and a slave diaphragm disposed in the slave chamber and which divides the slave chamber into first and second regions, wherein;

the main body inlet is adapted and configured to be connected to a compressed gas source;

the device outlet orifice is adapted and configured to direct a gas to a user for inhalation thereof via a device outlet;

the timing gas flow path extends from the main body inlet through the second region of the slave chamber, through the first region of the secondary slave chamber, and to the vent;

the demand gas flow path extends from the main body inlet through the primary chamber inlet orifice and the primary chamber and to a device outlet via the device outlet orifice;

the second region of the secondary slave chamber is in fluid communication with the device outlet via an outlet passage;

open and closed positions of the main diaphragm respectively allows and blocks a flow of gas from the second region of the slave chamber through the timing gas flow path, whose open position allows a flow of gas from the second region of the slave chamber through the timing gas flow path to the vent, the main diaphragm being moved from its closed position to its open position when a vacuum is applied to the device outlet; and open and closed positions of the slave diaphragm respectively allows and blocks a flow of gas from the primary chamber through the demand gas flow path, the slave diaphragm being moved from its closed position to its open position after the second region of the slave chamber has been partially depressurized from a pressure P1 to a pressure P2;

the main diaphragm is moved from its open position to its closed position after partial depressurization of the second region of the secondary slave chamber from pressure P2 to a pressure P3 and the slave diaphragm is moved from its open position to its closed position after repressurization of the second region of the slave chamber to a pressure above P2;

the gas demand device is adapted and configured to be operable in a cycle of first, second, third, fourth, and fifth consecutive phases;

at an expiration of the first phase and a commencement of the second phase, the slave chamber diaphragm and main diaphragm are in their closed positions to prevent flows of gas through the demand gas and timing gas flow paths, and pressures in the primary chamber and slave chamber second region are equal to a regulated pressure in the main body inlet;

in the second phase, a pressure in the slave chamber outlet orifice is sub-atmospheric because of a demand for gas at the device outlet orifice thereby placing the main diaphragm in its open position while the slave diaphragm remains in its closed position and allowing a flow of gas through the timing gas flow path while preventing a flow of gas through the demand gas flow path, a pressure inside the secondary slave chamber first region decreasing during the second phase;

the third phase commencing at an expiration of the second phase when a pressure in the slave chamber second region is decreased below a pressure in the slave chamber first region thereby placing the slave diaphragm to its open position while the main diaphragm remains in its open position and allowing a flow of gas through the timing gas and demand gas flow paths, a pressure inside the slave chamber first region decreasing during the third phase;

the fourth phase commencing at an expiration of the third phase when a pressure in the secondary slave chamber first region is decreased below a pressure applied by the spring thereby placing the main diaphragm in its closed position while the slave diaphragm remains in its open position to allow a flow of gas through the demand gas flow path and prevent a flow of gas through the timing gas flow path, a pressure inside the slave chamber second region increasing while the pressure inside the slave chamber first region is decreasing during the fourth phase;

the fifth phase commencing at an expiration of the fourth phase when a pressure in the slave chamber second region increases beyond that of the slave chamber first region thereby placing the slave diaphragm in its closed position while the main diaphragm remains in its closed position, pressure within the primary chamber increasing during the fifth phase;

the first phase commencing at an expiration of the fifth phase when pressure in the primary chamber builds to a level equal to the regulated pressure pressure in the main body inlet, the slave and main diaphragms remain closed to prevent flows of gas through the demand gas and timing gas flow paths;

the selectable orifice disk may be rotated in order to select an appropriately sized orifice that will yield a desired total volume of gas per minute to be delivered to a user; and the device outlet is in parallel fluid communication with both the secondary slave chamber second region and also the slave chamber first region.

* * * * *